United States Patent [19]

Streck

[11] 4,361,913

[45] Dec. 7, 1982

[54] INTRAOCULAR LENS

[76] Inventor: Donald A. Streck, 1725 Promenade, #701, Santa Monica, Calif. 90401

[21] Appl. No.: 250,612

[22] Filed: Apr. 3, 1981

[51] Int. Cl.³ ............................ A61F 1/16; A61F 1/24
[52] U.S. Cl. ......................................................... 3/13
[58] Field of Search ......................................... 3/13, 1

[56] References Cited

U.S. PATENT DOCUMENTS

| | | | |
|---|---|---|---|
| 4,159,546 | 7/1979 | Shearing | 3/13 |
| 4,242,760 | 1/1981 | Rainin | 3/13 |
| 4,249,271 | 2/1981 | Poler | 3/13 |
| 4,257,130 | 3/1981 | Bayers | 3/13 |

OTHER PUBLICATIONS

The Intraocular Implant Lens Development and Results with Special Reference to the Binkhorst Lens (Book) by M. E. Nordlohne, Second Edition, The Williams & Wilkins Company, Baltimore, 1975, pp. 14–20. Covered Bridge an Update on Lens Implantation (Book) by John H. Sheets, or Bridge Over Troubled Waters (3rd Attempt), 1977, pp. 4–13.

*Primary Examiner*—Ronald L. Frinks

[57] ABSTRACT

An intraocular lens suitable for implantation through a minimal width incision opening into either the anterior chamber or the posterior chamber. The lens incorporates three supporting members, at least one of which is a semi-flexible loop disposed adjacent a next support member to provide wide support while being compressable to an overlapped relationship to provide minimum width for insertion. The lens provides a limited degree of compressability to allow the lens to adapt to differing diameters of implantation location while, at the same time, providing sufficient rigidity so as to prevent undesired bowing.

7 Claims, 25 Drawing Figures

INTRAOCULAR LENS

BACKGROUND OF THE INVENTION

The present invention relates to intraocular lenses for implantation into living eyes following cataract removal and, more particularly, to intraocular lenses having deformable loops.

Figure 1:
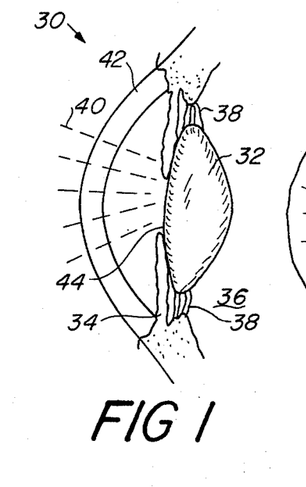
FIG. 1 is a cross-section through the front portion of a living eye.

A cross-section through the front portion of an eye, generally indicated as 30, is shown in FIG. 1. The natural lens 32 is suspended behind the iris 34 and in front of the vitreous 36 by zonules 38. Light, indicated by the dotted lines 40, passes through the cornea 42 and the pupillary opening 44 of iris 34 and thence through natural lens 32 to be focused on the retina (not shown).

Figure 2:
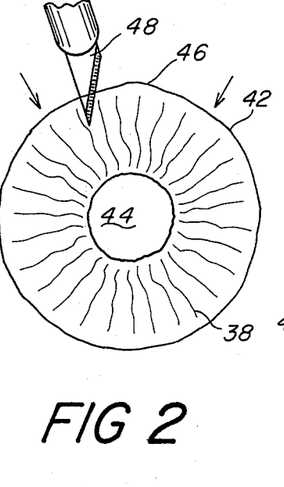
FIG. 2 is a front elevation view of the iris portion of an eye looking through the cornea.
Figures 3, 4:
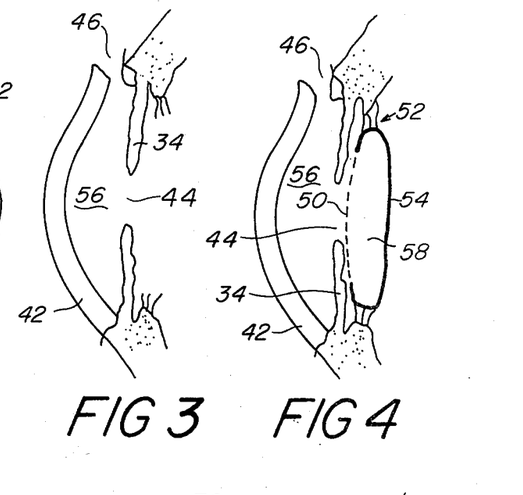
FIG. 3 is a side cutaway view through an eye following intracapsular lens extraction.
FIG. 4 is a cutaway view through the front portion of an eye following extracapsular lens extraction.

Sometimes, the natural lens 32 becomes cataractous so that light 40 no longer passes therethrough in a manner sufficient to create clear images. It is common practice to remove such a cataractous lens and provide light focusing by alternate means. As shown in FIG. 2, an incision opening 46 is made in the edge of the cornea 42 adjacent iris 34, as with scalpel 48. The incision opening 46 extends over an arc as indicated by the two arrows of FIG. 2. The natural lens 32 is withdrawn through the incision opening 46 by one of two commonly employed techniques. In one, the entire natural lens 32 is severed from the zonules 38 and removed leaving the forward portion of the eye 30 appearing substantially as shown in FIG. 3. Such a lens removal is referred to as an "intracapsular extraction". In the other technique commonly employed, the anterior portion, indicated as dotted line 50 in FIG. 4, of the capsular bag, generally indicated as 52, which is the outer covering of lens 32, is removed and the contents of capsular bag 52 forming lens 32 are removed. This leaves the posterior portion 54 of capsular bag 52 intact and supported by the zonules 38. The posterior portion 54 of capsular bag 52 supported by the zonules 38 thus forms a natural barrier to the vitreous 36. Such a lens extraction is referred to as an "extracapsular extraction".

The portion within the eye in front of the iris 34 and behind cornea 42 is referred to as the "anterior chamber" and is indicated as 56. The portion behind the iris 34 and in front of the posterior portion 54 of capsular bag 52 is referred to as the "posterior chamber" and is indicated as 58.

Originally, following cataract extraction, the patient was required to wear thick glasses in order to see. The thick glasses, in addition to being heavy and unsightly, caused a magnification such that correction on only one eye was impractical. Later, in some cases, patients without a natural lens were able to use a contact lens to perform the function of the missing natural lens. Unfortunately, in the age group most prone to cataract, many patients are not able to wear or insert a contact lens.

In 1948, following World War II, a British opthamologist, Dr. Harold Ridley, was inspired to form a lens of plastic and insert it within the eye as a replacement lens. It had been found during the war that plastic material, as employed in the canopies of airplanes, which penetrated the eye was tolerated within the eye as a foreign body substance. Dr. Ridley's lens (55 in FIG. 5) was merely a disc of plastic ground to the desired optical focusing characteristics which was then placed within the posterior chamber 58 following an extracapsular extraction. The lens was intended to be held in place by entrapment between the surrounding tissues, and hopefully, by the formation of adhesions thereto. While the lens worked well in many cases, the complication rate, primarily from dislocation due to the heavy weight of the lens and the lack of positive fixation in most cases, led to much research directed at developing an intraocular lens design having a more acceptable complication rate.

To this end, in the early 1950's, emphasis shifted from the posterior chamber 58 to the anterior chamber 56, first with the Strampelli lens and later with the Choyce modifications of that basic lens design. These were rigid anterior chamber lenses such as that indicated as 60 in FIG. 6. Anterior chamber lenses according to this original design are substantially flat ribbons of plastic having a lens formed in the center thereof. Small feet 62 are formed in the ends thereof and adapted to lodge in the angle between the iris 34 and the cornea 42. Being rigid, these anterior chamber lenses cannot adapt to differences in diameter across the angle of the anterior chamber 56. Accordingly, the tip to tip dimension "d" became, and is, critical. If the length is too long, the feet 62 dig into the delicate tissue adjacent the angle containing major blood vessels of the eye. This can lead to severe problems. If the lens is too short, it can move about, and may even rub and cause damage to the highly delicate endothelium lining the inside of the cornea 42. In either case, the actual implantation must be done with extreme care as the rigid lens can cause damage to the delicate tissue of the eye if thrust into position too boldly. If the iris tissue is caught by the advancing leading edge of the lens during insertion, the iris can be sheared off.

The Choyce type anterior chamber lens according to a variation of this original concept are still very popular. Under some circumstances, a lens cannot be placed with portions in the posterior chamber. In many of these cases, and in the case of personal preference by many surgeons, anterior chamber lenses are still often used. An intraocular lens can be implanted at the time of cataract removal (primary implantation) or at a later time (secondary implantation). Anterior chamber lenses are very popular for secondary implantations. During such a secondary implantation, it is highly desirable to minimize the size of the incision made in the cornea as the longer the incision, the longer the healing process that can be expected. If the incision is small, a secondary implantation becomes almost minor surgery. Despite their continued popularity, however, anterior chamber lenses had, and still have, limitations associated with them.

In the early 1950's, the problems of rigid anterior chamber lenses were already recognized and attempts were made to correct them. For one, even when sized correctly, (i.e. the proper tip-to-tip length for the diameter of the location), a rigid anterior chamber lens, such as that indicated as 60 in FIG. 6, creates what is known as a "tender" eye. That is, as one rubs the eye or the eye tends to deform from natural movement, the rigid lens 60 creates internal localized pressure at the edge of the eye causing various sensations to the wearer. This has been described as "itching", "pain", or the feeling of "having something in the eye".

Figures 5, 6, 7, 8, 9, 10, 11, 12:
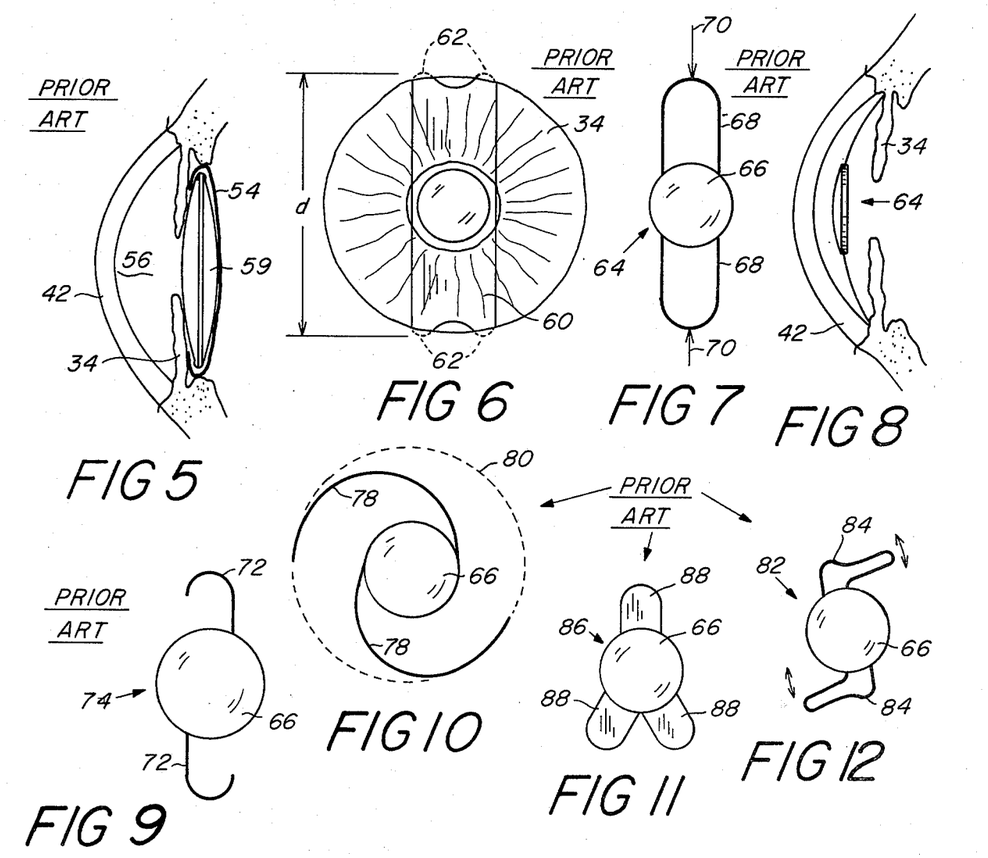
FIG. 5 is a cutaway elevation through the front portion of an eye showing a Ridley type posterior chamber lens in place.
FIG. 6 is a front elevation showing an anterior chamber lens of the Choyce type in place.
FIG. 7 is a front elevation of a Dannheim type lens.
FIG. 8 is a side cutaway elevation of the front portion of an eye showing an overlength Dannheim lens in place undergoing bowing thereof.
FIG. 9 is a front elevation of a Barraquer type lens having open compressible loops of a generally J-shape.
FIG. 10 is a front elevation of an incomplete compressible loop Simcoe type lens having broad sweeping loops.
FIG. 11 is a rigid Ridley/Pearce type lens having three supporting tab members as originally implanted by Ridley in the anterior chamber and more recently by Pearce into the posterior chamber within the capsular bag.
FIG. 12 is a front elevation view of a Sheets type lens having complete loops configured to perform in the compressive manner of incomplete loops in order to give four-point suspension when implanted within the capsular bag.

One of the earliest attempts to solve the problem of the pressures of a rigid lens and the need to have the rigid lens available in varying lengths was the Dannheim type lens. Such a lens is generally indicated as 64 in FIG. 7. The Dannheim lens 64 comprised a plastic lens body 66 having a pair of opposed, closed, nylon loops 68 extending therefrom. The intent was that the nylon loops 68, being flexible, would compress to allow the lens 64 to adapt to differing diameter eyes. Unfortunately, it is characteristic of a closed flexible loop, such as loops 68, that when longitudinal pressure is applied, as indicated by the arrow 70, the loops will bow out of the plane of the lens body 66 rather than compressing in the plane of the lens body 66 as necessary to accomplish the desired objective. Accordingly, overlength Dannheim lenses 64 typically assumed a position such as shown in FIG. 8. Thus disposed, it was highly prone to touch the delicate endothelium lining the cornea 42, with attendant complications. Moreover, the lens 64 was suspended essentially by the two points adjacent arrows 70, such that a spindle effect was created whereby the lens could rotate about its longitudinal axis creating further problems.

One of the pioneers of intraocular lens design was Dr. Joaquin Barraquer of Barcelona, Spain. Dr. Barraquer was enamoured of the concept of elastic or compressable lenses and did much work with Dannheim lenses and, later, with compressible lenses of his own design. Dr. Barraquer found that if the loops 68 of a Dannheim lens 64, as shown in FIG. 7, were cut to form two incomplete J-shaped loops 72 extending from lens body 66, a lens, generally indicated as 74 in FIG. 9, would be created which resisted the bowing upon the application of longitudinal forces and which, moreover, was highly compressible in the plane of the lens body 66.

The Barraquer lens 74 of FIG. 9 achieved the objective of being compressible so as to adapt to differing diameters of eye and, additionally, was so highly compressible so as to avoid the problems of internal pressure on tissue created by the rigid lenses. Unfortunately, the Barraquer lens 74 was unsuccessful as an anterior chamber lens for a number of reasons which can be surmised from an engineering and medical evaluation of the lens. First, the incomplete loops 72 were too compressible, such that the lens was free to move about as a result of normal movements of the patient. As with the Dannheim lens 64, the Barraquer lens 74 was suspended by two points so as to be prone to the pivoting or spindle action about the longitudinal axis. Moreover, the loops 72 were not in contact with tissue which would form adhesions which would then hold the lens in place. As a result, the total fixation was by the insufficient outward pressure of the loops 72. That is, the loops 72 were compressible to adapt to different diameters and did not create harmful forces, but, on the other hand, did not create sufficient force to hold the lens in place. Last, the loops were formed of nylon which tended to absorb moisture from the environment of the living eye and, therefore, degraded over a period of time.

Recently, the Barraquer lens design has had a revitalization as a posterior chamber lens. When implanted into the posterior chamber 58 with polypropylene substituted for nylon in the loops 72, the problems associated with that lens as an anterior chamber lens are eliminated for the most part. The Barraquer type lens 74 is implanted in the posterior chamber 58 following an extracapsular extraction. Thus, the lens body 66 is trapped between the iris 34 and the posterior 54 of capsular bag 52. The loops 72 themselves can be placed within the remnants of the capsular bag 52, outside of it, or one in and one out. Typically, adhesions will form to lens 74 and loops 72 to further fixate the lens in position.

Further refinements of the basic Barraquer lens 74 have been made available recently for use in the posterior chamber. In the Simcoe type lens, generally indicated as 76 in FIG. 10, the lens body 66 has a pair of long sweeping compressible loops 78. This lens design, developed by Dr. C. William Simcoe, is adapted to contact the area into which the lens is fixated, as indicated by the dotted circle 80, continuously at many points to eliminate the single point suspension with attendant pivoting and, simultaneously, distribute the pressure over more than one point.

The lens 82 of FIG. 12 was developed (and is indicated as presently in the process of being patented) by Dr. John Sheets. It has a pair of compound curved closed loops 84 and is specially designed to be implanted within the remnants of the capsular bag 52 following extracapsular extraction. The closed loops 84 operate in the manner of the loops 72 of the Barraquer lens 74 of FIG. 9 except that the bending is concentrated in preselected locations by the configuration of loops 84 and the resultant pressure against the edges of the remnants of the capsular bag 52 is at four points instead of two points.

Several other lens designs remain viable in the art at this time. For example, the later Ridley or Pearce lens 86 of FIG. 11 is formed of a solid piece of plastic such that there is a lens body portion 66 with three flat tab support members 88 radiating therefrom. This design of Dr. John Pearce with both two and three tab variations is presently being implanted in the posterior chamber within the capsular bag both with and without sutures for fixation.

The Copeland or Maltese Cross type lens is a solid plastic lens having four tab extensions radiating at 90° intervals from the lens body. It is implanted in the pupilary opening of the iris with two opposed tabs on one side of the iris and the other two tabs on the other side.

Figures 13, 14, 15, 18:
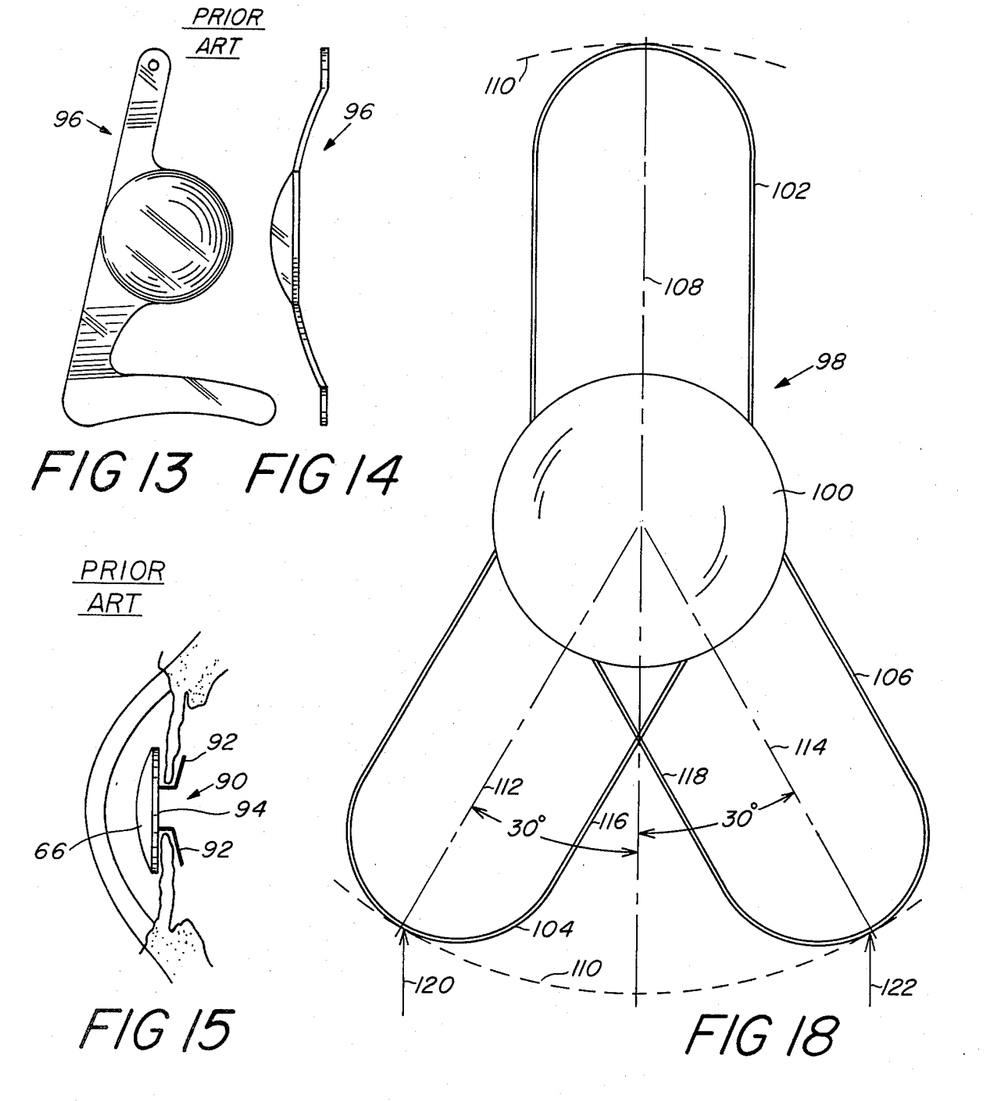
FIGS. 13 and 14 are front and side elevation views of Kelman type lens.
FIG. 15 is a cutaway front elevation through a portion of an eye showing an irido-capsular lens in place.
FIG. 18 is a front elevation of a lens according to one embodiment of the present invention.
Figure 16:
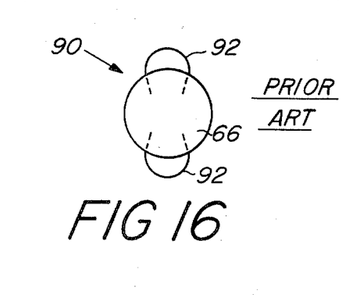
FIG. 16 is a front elevation of a two-loop Binkhorst type irido-capsular lens.
Figure 17:
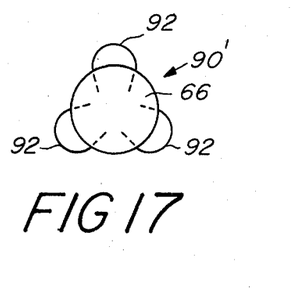
FIG. 17 is a front elevation of a three-loop Federov type irido-capsular lens.

Yet another type of lenses employing flexible loops are classified as irido-capsular lenses and are, for the most part identified with Drs. Binkhorst, Worst, and Federov. A typical example of such a lens, generally indicated as 90, is shown in FIG. 15. Whereas the lenses heretofore described have the supporting portions or loops radiating laterally outward from the edges of the lens body 66 with the supporting pressure on their extreme ends, in the irido-capsular lens 90, the loops 92 extend outward normal to the posterior surface 94 of lens body 66 from a point between the center and outer edge thereof. The loops 92 are normal to the posterior surface 94 for a distance sufficient to pass from the anterior side of iris 34 to the posterior side of iris 34 and then angle substantially parallel to the posterior side of iris 34 whereupon when placed as shown in FIG. 15, iris 34 is entrapped between the posterior surface 94 and the loops 92. The irido-capsular lenses 90 typically come with two loops (Binkhorst two-loop type) as shown in FIG. 16 or three loops (Federov type) as shown in FIG. 17. There are additional variations, not shown, on this basic theme including additional loops (Binkhorst four-loop type) or staves (Federov "Sputnik" type) radiating from the edge of the lens body 66 to provide additional support area to prevent the lens 90 from dislocating from its position within the pupilary opening 44 upon wide dilation of the iris 34.

Despite all the variations heretofore described, each is a trade-off on desirable features that one would incorporate in an intraocular lens if possible. As can be seen, previous lens designs have been suitable for location within the anterior chamber or the posterior chamber, but not both. As mentioned, it is highly desirable to minimize the size of the incision opening 46 inasmuch as the greater the length of the incision opening 46, the greater the healing process which must take place. The actual passage of the lens through the incision opening 46 during the implantation process must be accomplished in a manner such as to minimize trauma to the adjacent endothelial cells lining the cornea. The basic structure should provide a broad support resistive to rotational movement, be firm enough to maintain the lens in position, yet be resilient enough to prevent damage to the tissue in contact.

Recently, a lens has been introduced which is a different compromise to certain of the aforementioned criteria not previously addressed. This lens is shown in FIGS. 13 and 14 and is the subject of U.S. Pat. No. 4,092,743 to Dr. Charles Kelman. The Kelman lens, generally indicated as 96, is an anterior chamber lens designed to be inserted through a minimum width incision opening 46 while providing a broad support base. Its primary intent is as a replacement for the Choyce type rigid lens 60 of FIG. 6 which can be implanted through a narrow incision opening 46 but which, by contrast, has a narrow supportive area. The Kelman type lens 96 of FIGS. 13 and 14 is generally in the shape of a "7" with the lens body carried on the vertical member. For this reason, it is sometimes referred to as the "pregnant 7" lens. It is a one-piece, solid plastic lens designed to be "snaked" through the narrow incision opening. As with the lens 60 of FIG. 6, however, it is basically a rigid lens and, therefore, must be sized to the diameter. Moreover, while a degree of flexibility is claimed for the lens design (and apparently achieved, at least as compared to the Choyce type lens design according to tests conducted on the two lenses) so as to be less causing of sensitivity within the eye than the Choyce type design it is intended to replace, the virtual rigid nature of the lens still does not achieve the complete lack of sensitivity obtained by elastic loops.

Wherefore, it is the object of the present invention to provide an intraocular lens design which can be used both as an anterior chamber lens and a posterior chamber lens.

It is a further object of the present invention to provide an intraocular lens having a broad support base which can be implanted through a minimum width incision opening.

It is yet another object of the present invention to provide an intraocular lens design which is compressible in its overall tip-to-tip length sufficiently to adapt to changes in diameter of the area of placement of the order of one to two millimeters and compressible to a degree such as to virtually eliminate tenderness when placed in the anterior chamber and/or damage to contacted tissue while being sufficiently rigid to resist bowing and other movements which have heretofore rendered compressible lenses unacceptable for placement in the anterior chamber.

SUMMARY

The foregoing objectives have been met by the intraocular lens of the present invention which comprises a lens body portion and at least three support members connected to the body portion and extending radially outward therefrom with no two having a common longitudinal axis. At least one of the support members is disposed adjacent to one other of the support members in a position of angular relationship thereto of between 40° and 90°. The one member is biased to the angular position and is further deformable towards the one other member to a position wherein the combined width of the one member and the one other member is no greater than the width of the lens body portion. In the preferred embodiments, the adjacent edges of the one member and one other member are in overlapped relationship. Further, the one member is a closed loop of flexible filament material being of sufficient thickness to resist bowing out of the plane of the loop from forces along the longitudinal axis but sufficiently thin to deform in the plane of the loop as a result of forces at an angle to the longitudinal axis.

DESCRIPTION OF THE DRAWINGS

FIGS. 5 through 17 depict lenses according to the prior art wherein:

DESCRIPTION OF THE PRESENT INVENTION AND ITS VARIOUS EMBODIMENTS

Turning now to FIG. 18, a lens, generally indicated as 98, is shown embodying the present invention. Lens 98 comprises a lens body 100 having three supporting members 102, 104, 106 extending laterally from the edge thereof. In the particular embodiment of FIG. 18, all three support members 102, 104, 106 are closed loops of flexible filament type material such as polypropylene which can be conveniently attached to the lens body 100 by edge drilling body 100, inserting the free ends of members 102, 104, 106, therein, and affixing them therein by a so-called "staking" process well known in the art wherein the material of lens body 100 is compressed under pressure against the members 102, 104, 106 to grip them firmly within body 100. Other methods, of course, could be used to attach the ends of members 102, 104, 106 to lens body 100 within the scope and spirit of the present invention.

As the lens 98 of FIG. 18 is viewed, a center line 108 represents the vertical axis of the patient's eye and the dotted circular portions 110 represent the outer boundaries of the area into which the lens is to be placed. For example, circle 110 could be the angle between the cornea and iris if the lens 98 is placed into the anterior chamber or could be the angle posteriorally of the iris or the outer periphery of the capsular bag if the lens 98 is placed into the posterior chamber. While deviations are, of course, possible according to the wishes of the implanting surgeon, it is primarily the intent of the lens design described herein that support member 102 be facing in the vertical direction and members 104, 106 subtend angles on either side of the vertical in the downward direction (i.e. towards the patient's feet). The two lower support members 104, 106, each subtend angles on either side of the vertical as previously mentioned. The longitudinal axis of member 104 is indicated at 112 and the longitudinal axis of member 106 is indicated as 114. As indicated, the preferred deviation from the center line 108 for members 104, 106 is 30° so that the two members 104, 106 subtend a total arc of 60°. While a 60° arc is preferred, acceptable operation is anticipated with a subtended total angle as small as 40° or as large as 90°.

It will be noted that the adjacent edges 116, 118 are in overlapped relationship. Such a relationship gives preferred performance in that the lower support members 104, 106 can be compressed towards one another so as to provide a minimum overall width while, at the same time, providing mutual support in resistance of any bowing.

Insofar as loops are employed in the various embodiments of the present invention, it will be noted that at least one of the two lower support members 104, 106 is always of a flexible filament type material. It is preferred that the loops be of polypropylene and that they be of a thickness to give the desired combination of characteristics. That is, they should be thick enough so as to resist bowing under compressive forces towards the lens body 100 along center line 108 and axes 112, 114. On the other hand, they should be thin enough to allow deflection from force vectors at an angle to the axes 112, 114. It should be noted that as constructed, there are three loops and no two have a common longitudinal axis. When positioned within the eye, therefore, a force, for example towards the lens body 100 along center line 108 which is also the longitudinal axis of support member 102, will be countered by force vectors 120, 122 on loops 104, 106, respectively. Force vectors 120, 122, therefore, will tend to deform loops 104, 106 away from each other in the planeof lens body 100. Investigation will show that a similar reaction will be obtained as a result of longitudinal forces along axes 112 or 114 of the two lower members 104, 106. Thus, by proper selection of the flexing characteristics of the filament material comprising loops 102, 104, 106 in combination with the physical relationship of loops 102, 104, 106 as shown, lens 98 is capable of slight compression along center line 108 to accommodate minor differences in the diameter of the area defined by circle 110 and to "give" from eye movement or rubbing so as to eliminate the tenderness of normal rigid lenses while, at the same time, being sufficiently rigid so as to resist the bowing effect and undesired movement within the anterior chamber which was characteristic of the the Dannheim and Barraquer type lens designs discussed under "Background of the Invention".

Figures 19, 20, 21:
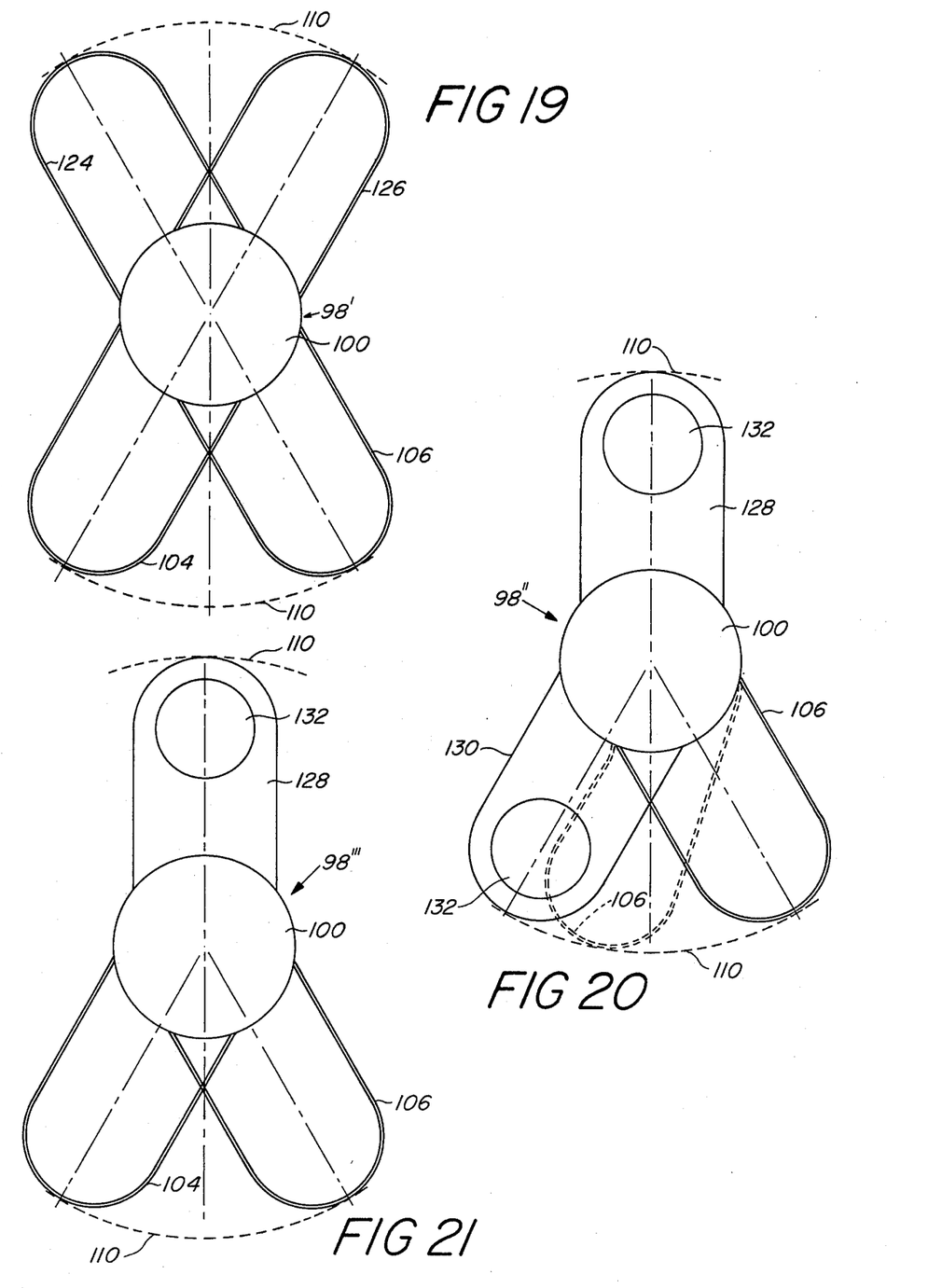
FIG. 19 is a front elevation of a lens according to the present invention in a second embodiment.
FIG. 20 is a front elevation of a lens according to the present invention in a third embodiment.
FIG. 21 is a front elevation of a lens according to the present invention in a fourth embodiment.

Several other lens embodiments according to the present invention are shown in FIGS. 19 through 21. In FIG. 19, the overlapping loop arrangement is mirrored in the upper support members wherein the single vertical loop 102 is replaced by a pair of overlapped angulated loops 124, 126 in the lens generally indicated as 98'. The embodiment of FIG. 19 is particularly well suited for placement within the capsular bag as a replacement for the Sheets type lens of FIG. 12 so as to provide the same four-point suspension, which tends to stretch out the posterior surface of the capsular bag. It also provides for a four-point suspension when implanted within the anterior chamber, which provides increased stability at a sacrifice of ease of removal should this become required. As can be understood, the embodiment of FIG. 19 would have the lower loops 104, 106 passed through the incision opening in a manner to be described in detail hereinafter. The upper loops 124, 126 would then be compressed toward one another by the edges of the wound opening as the lens is advanced and snap apart into position after passing through the incision opening.

FIG. 20 is an embodiment providing the utmost rigidity of the various embodiments shown. The lens, generally indicated as 98", comprises a lens body 100 and an upper rigid tab 128 and a lower rigid tab 130 of unitary construction. The angular relationship of body 100, upper rigid tab 128, and lower rigid tab 130 are as previously described with relationship to the flexible loops of the embodiment of FIG. 18. Holes 132 through tabs 128, 130 are optional and can be provided for gripping by instruments or suturing, as well-known in the art. The single moveable lower support member 106 is provided as with the other embodiments. As can be seen by the dotted representation shown in FIG. 20, to realize the benefits of the present invention, only one moveable support member is necessary. In the implantation process to be described, member 106 is deflected towards tab member 130 in overlapped relationship until the total width of members 130, 106 is equal to the width of the incision opening through which the lens is to be passed which, typically, is desired to be only slightly larger than the diameter of the lens body 100.

A compromise embodiment is shown in FIG. 21. Lens 98''' thereof has the single upper rigid tab 128 in unitary construction with the lens body 100 but with the two deformable lower loops 104, 106 as previously described in relationship to the embodiments of FIGS.

18 and 19. This particular embodiment provides the rigidity between the upper tab 128 and lens body 100 to allow manipulation by gripping the rigid tab 128 during implantation with the improved compressibility provided by having the two lower members 104, 106 both be deformable loops.

Figure 22:
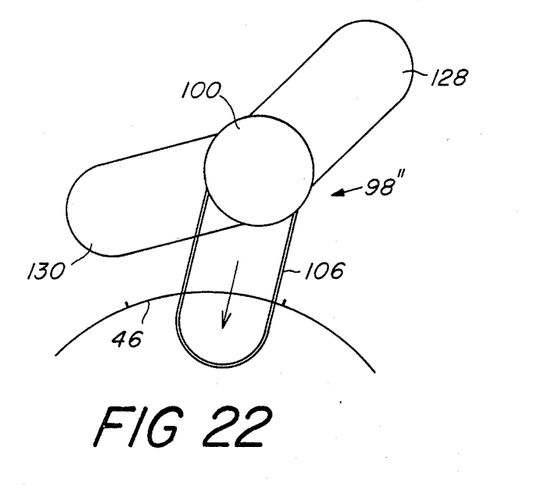
FIGS. 22–25 show the steps employed in passing a lens embodying the present invention through a minimum width incision opening.
Figure 23:
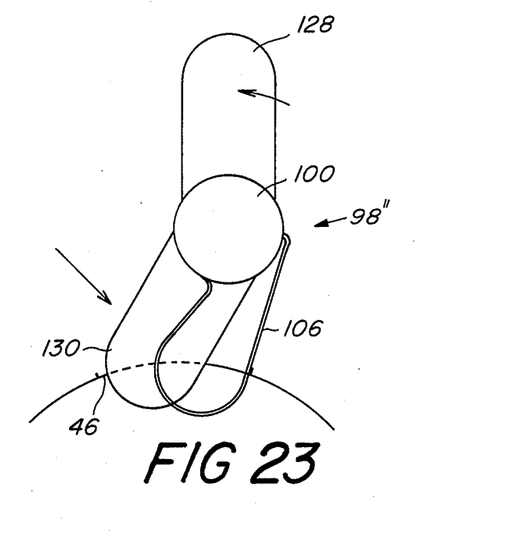
Figure 24:
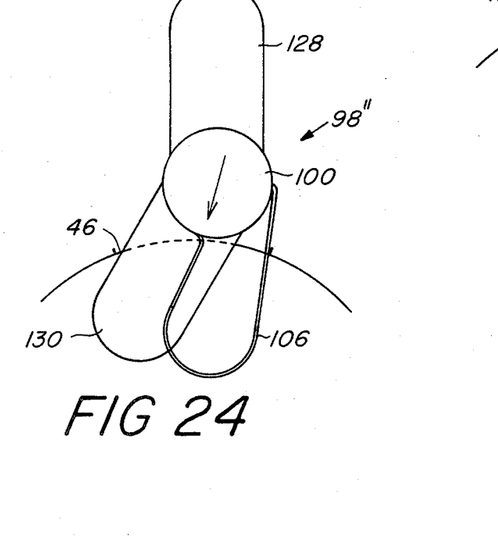
Figure 25:
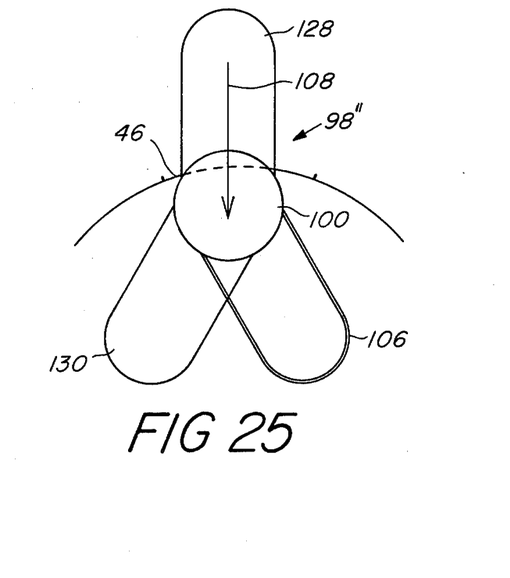

Turning now to FIGS. 22 through 25, the method of inserting the lens of the present invention, as typified by the lens 98" of FIG. 20, is shown. In FIG. 22, the implantation through the incision opening 46 is begun by inserting the lower portion of flexible member 106 into the wound opening 46 to a point past the curved portion thereof so that a compressive force can be applied to loop 106 by the side of wound opening 46. By rotating lens 98" about the center of lens body 100 as shown in FIG. 23, loop 106 is compressed towards rigid lower tab 130 until the total width at the widest point is narrow enough to pass through the wound opening 46. As then shown in FIG. 24, lens body 100 is pushed through the incision opening 46 along a line bisecting rigid tab 130 and loop 106 until the lens body 100 has passed through the incision opening 46 a sufficient distance to allow loop 106 to resume its normal angulated position to tab 130 due to the biasing effect of the material from which it is constructed. The remaining portion of lens body 100 and upper tab 128 can then be pushed through the incision opening along the longitudinal axis 108 of upper tab 128 in the usual manner, and the balance of the implantation is according to techniques well-known to those skilled in the art.

Wherefore, from the preceding description, it should be apparent to those skilled in the art that the intraocular lens of the present invention in its various embodiments all provide the desired objectives over the prior art in varying degrees. In particular, all the embodiments are compressible along their longest dimension to a degree sufficient to allow for minor variations in the overall diameter of the space into which they are to be implanted. Moreover, the lenses have sufficient "give" to be non-damaging to delicate tissue so as to provide for an untender eye and adapt during eye movement and rubbing from outside stimulus. Further, they are implantable through a minimum width incision opening only slightly wider than the width of the lens body while, at the same time, providing a wide radius of support once in the area of implantation. Moreover, the lens design is such as to be sufficiently rigid and adaptable to be used in both the anterior and posterior chambers of the eye both within the capsular bag and out of it.

Having thus described my invention, I claim:

1. An intraocular lens adapted to compress in width for insertion through an incision opening of minimal width and having a degree of longitudinal compressability for safety and size adaptation, said lens comprising:
   (a) a lens body portion;
   (b) at least three support members connected to said body portion and extending radially outward therefrom with no two of said members having a common longitudinal axis, at least one of said support members being disposed adjacent one other of said support members in a position of angular relationship thereto of between 40° and 90°, the adjacent edges of said one member and said one other member overlapping one another at an angle of between 40° and 90° adjacent said lens body portion, said one member being biased to said angular position and further being deformable towards said one other member to a position wherein the combined width of said one member and said one other member is substantially no greater than the width of said lens body portion.

2. The lens of claim 1 wherein:
said one member and said one other member are closed loops of flexible filament material being of sufficient thickness to resist bowing out of the plane of the loop from forces along their longitudinal axes but sufficiently thin to deform angularly in the plane of the loop as a result of forces at an angle to their longitudinal axes.

3. The lens of claim 2 wherein:
said third one of said members is a closed loop of flexible filament material being of sufficient thickness to resist bowing out of the plane of the loop from forces along its longitudinal axis but sufficiently thin to deform angularly in the plane of the loop as a result of forces at an angle to its longitudinal axis.

4. The lens of claim 3 werein:
there are four said support members and the two other members after said at least one and said adjacent one have one thereof disposed adjacent the other in a position of angular relationship thereto of between 40° and 90° with the adjacent edges thereof being overlaped and at an angle of between 40° and 90° adjacent said lens body portion and being biased to said angular position and further being deformable towards one another to a position wherein the combined width of said two members is substantially no greater than the width of said lens body portion.

5. An intraocular lens adapted to compress in width for insertion through an incision opening of minimal width and having a degree of longitudinal compressability for safety and size adaptation, said lens comprising:
   (a) a rigid portion comprising a central lens portion having a pair of tab members radiating therefrom in the plane of said central lens portion, said tab members being dispoed with respect to one another such that one lies along a longitudinal axis passing through the center of said central lens portion and the other forms an angle of between 160° and 135° with respect to said one and correspondingly an angle of between 20° and 45° with respect to said longitudinal axis; and,
   (b) a support member connected to said body portion and extending radially outward therefrom adjacent said other of said tab members in a position of angular relationship thereto of between 40° and 90°, said support member and said other of said tab members overlapping one another at an angle of between 40° and 90° adjacent the periphery of said central lens portion, said support member being biased to said angular position and further being deformable towards said other tab member to a position wherein the combined width of said support member and said other tab member is substantially no greater than the width of said central lens portion, said support member being a closed loop of flexible filament material of sufficient thickness to resist bowing out of the plane of the loop from forces along its longitudinal axis but sufficiently thin to deform angularly in the plane of the loop as a result of forces at an angle to its longitudinal axis.

6. In an intraocular lens having a lens body portion and at least a pair of supporting members extending outward therefrom, the improvement for allowing the lens to compress in width for insertion through an incision of minimal width and for imparting a degree of compressability to the lens for safety and size adaptation comprising:

(a) said supporting members being disposed adjacent one another in a position of angular relationship of between 40° and 90°, said supporting members overlapping one another at an angle of between 40° and 90° adjacent the lens body portion, one of said support members being biased to said angular position and further being deformable towards the other supporting member to a position wherein the combined width of said supporting members is substantially no greater than the width of the lens body portion, said deformable supporting member being a closed loop of flexible filament material of sufficient thickness to resist bowing out of the plane of the loop from forces along its longitudinal axis but being sufficiently thin to deform angularly in the plane of the loop as a result of forces at an angle to its longitudinal axis.

7. The method of implanting an intraocular lens having a lens body portion with three support members connected to the body portion and extending radially outward therefrom with one support member being disposed adjacent one other support member in a position of angular relationship thereto of between 40° and 90° with the adjacent edges of the one member and the one other member overlapped at an angle of between 40° and 90° adjacent the lens body portion with the one member being a closed loop of flexible filament material of sufficient thickness to resist bowing out of the plane of the loop from forces along its longitudinal axis but sufficiently thin to deform angularly in the plane of the loop as a result of forces at an angle to its longitudinal axis through an incision in the edge of the cornea into the anterior chamber of a living eye comprising the steps of:

(a) inserting the one member into the incision;
(b) compressing the one member towards the one other member against the edge of the incision until the combined width of the two members is sufficiently narrow to pass through the incision;
(c) rotating the lens to align both of the members in the incision; and,
(d) inserting the members through the incision followed by the lens body and the third support member.

* * * * *